United States Patent [19]

Albrektsson

[11] Patent Number: 4,917,703
[45] Date of Patent: Apr. 17, 1990

[54] BONE INGROWTH CHAMBER

[75] Inventor: Tomas Albrektsson, Mölndal, Sweden

[73] Assignee: Nobel Pharma AB., Sweden

[21] Appl. No.: 124,148

[22] Filed: Nov. 23, 1987

[30] Foreign Application Priority Data

Nov. 21, 1986 [SE] Sweden ................. 8604974

[51] Int. Cl.⁴ .......................... A61F 5/00; A61F 2/28
[52] U.S. Cl. .......................... 623/66; 623/16
[58] Field of Search ................. 623/16, 17, 10, 12, 623/14, 66; 128/92 R, 92 W, 92 YG; 433/173, 176

[56] References Cited

U.S. PATENT DOCUMENTS

| | | | |
|---|---|---|---|
| 3,514,791 | 7/1967 | Sparks | 623/12 X |
| 4,330,891 | 5/1982 | Branemark | 623/16 |
| 4,645,504 | 2/1987 | Byers | 623/10 |

FOREIGN PATENT DOCUMENTS 2134335 8/1984 United Kingdom ............ 623/10

OTHER PUBLICATIONS

Biomaterials and Biomechanics, 1983, pp. 238–288, Elsevier Science Publishers B.V., Amsterdam, NL; T. Albretsson et al.; "The Harvest Chamber—A Newly Developed Implant for Analysis of Bone Remodelling in Situ".
Acta Radiolagica Oncology, vol. 25, No. 1. 1986, pp. 27–62, Gothenburg, SE; M. Jacobsson et al.; "Provided Repetitive Healing of Mature Bone Tissue Following Irradiation".
Acta Oncologica, vol. 26, No. 1, 1987, pp. 63–63, Gothenburg, SE; P. Kalebo et al.: "Bone Healing Following Irradiation During Tourniquet Ischaemia".
P-I Branemark et al., "Osseointegrated Titanium Fixtures in the Treatment of Edentulousness", —Biomaterials, 1983, vol. 4, Jan.
Richard Skalak, "Biomechanical Considerations in Osseointegrated Prostheses". The Journal of Prosthetic Dentistry, Jun. 1983, vol. 49, No. 6.

Primary Examiner—Alan W. Cannon

[57] ABSTRACT

An apparatus for studying tissue ingrowth in an implant under different experimental conditions, in particular in response to locally administered test substances is made of a bio-compatible material, preferably pure titanium, and is implanted in living bone tissue, primarily for animal experimental activities. The apparatus includes an outer portion with a central recess in which an inner portion is inserted. In the assembled state, the two portions form at least two bone ingrowth through channels which are exposed when the inner portion is dismounted, for comparative examination of the bone ingrowth promoting/retarding properties of test substances disposed in at least one of the channels.

5 Claims, 2 Drawing Sheets

BONE INGROWTH CHAMBER

TECHNICAL FIELD

The present invention relates to an apparatus for studying bone ingrowth in an implant in response to a locally administered test substance. The apparatus is primarily intended for use in animal experimental activities, but a certain clinical, experimental use may also occur. The apparatus is of a biocompatible material, preferably titanium, and is intended to be implanted in living bone tissue.

BACKGROUND ART

It is previously known in this art how artificial implants may be anchored directly in bone tissue. In order to avoid the risk of loosening or detachment, every attempt is made to achieve a direct contact, that is an exact adaptation between the implant and the surrounding bone tissue, so-called osseointegration. Such exact adaptation may be achieved by sophisticated operational technique and by a suitable design of the implant. The osseointegration principle developed by professor Brånemark et al has successfully been used clinically for 20 years for maxillary-anchored dental bridges and is described in, for example:

P-I Brånemark et al, "Osseointegrated titanium fixtures in the treatment of edentulousness". Biomaterials, 1983. Vol 4, January; and Rickard Skalak, "Biomechanical considerations in osseointegrated prostheses". The Journal of Prosthetic Dentistry, June 1983, Volume 49, Number 6.

The principle is based on the fact that the implant is of pure titanium, at least in the interface zone between living tissue and implant. Swedish patent specification No. 79.02035-0 corresponding to U.S. Pat. No. 4,330,891 also discloses and describes the importance of the surface structure of the titanium for a powerful connection between the living bone tissue and the implant. By a special so-called microporous surface structure of the implant, the preconditions are further improved for a more or less permanent anchorage of the implant in the tissue.

To be able to assess the preconditions and potential for different implants to form a permanent anchorage with the tissue, there is a need to be able to study in greater detail and under standardized conditions the bone ingrowth of the implant and also those phases which precede the bone formation proper. Thus, it is previously known in this art how a special examination chamber may be operated into the bone tissue of a living animal, the chamber being designed such that samples of newly-formed bone tissue may be harvested from the chamber at regular intervals, and be examined. Hence, the chamber makes possible a quantification of bone ingrowth/implant incorporation under different experimental conditions without the need of sacrificing the animal. Such a test chamber, "The Harvest Chamber", is described in T. Albrektsson, M. Jacobsson and P. Kälebo, "The Harvest Chamber—A newly developed Implant for Analysis of Bone Remodelling in situ", Biomaterials and Biomechanics 1983, pp. 283-288.

The harvest chamber is constructed from an outer portion with a central recess in which an inner, removable portion is inserted. The two portions together form a bone ingrowth through channel which is intended to be exposed when the inner portion is removed in order, by such a manner, to make possible examination of tissue which has grown into the channel.

With the assistance of the harvest chamber, the bone ingrowth may be studied under different pathological-/experimental conditions and be compared with bone formation under normal conditions. For comparative tests, one examination chamber is normally inserted surgically into each extremity, for example the tibia, of the experimental animal. The one chamber acts as a test chamber and is surgically placed in that bone tissue which is exposed to, or will be exposed to, a potentially bone-stimulating/bone-retarding effect of some type, for example a locally administered test substance, while the second chamber constitutes a control reference chamber and is surgically inserted into bone tissue which is not under such influences. Evaluation of the results is affected in that bone ingrowth in the test chamber inserted in the one extremity is compared with bone ingrowth in the control reference chamber in the other extremity. Suitably, data-based microradiography is employed for quantification.

While the difference between the bone tissues, including their growth capacity, is slight under normal conditions, see for example the reference "The Harvest Chamber . . . ", FIG. 2, differences in the bone tissue between the two extremities may, in certain cases, derange the result of the evaluation.

OBJECT OF THE PRESENT INVENTION

The object of the present invention is, therefore, to realize an apparatus which permits comparison of bone ingrowth under as similar conditions as possible. To this end, the invention is based on the fact that one and the same test chamber may be employed for simultaneous comparative tests. The apparatus of the present invention includes an outer portion with a central recess and a removable inner portion inserted in the recess, these portions together forming at least two separate bone ingrowth channels which are intended to be exposed when the inner portion is removed, for comparative examination of the bone ingrowth promoting/retarding properties of test substances disposed in one or more of the channels.

In a first embodiment of the present invention, the bone ingrowth channels consist of two discrete through channels, one of the channels having been prepared with the test substance in question.

In a second embodiment of the present invention, the channels adopt a Y-shaped pattern, in which case comparison can be made between test substances disposed at the prong ends of the Y.

BRIEF DESCRIPTION OF THE ACCOMPANYING DRAWINGS

The nature of the present invention and its aspects will be more readily understood from the following brief description of the accompanying Drawings, and discussion relating thereto.

In the accompanying Drawings:

FIG. 1 illustrates the first embodiment of the present invention with two discrete through channels; and FIG. 2 illustrates the second embodiment of the present invention in which the channels form a Y-shaped pattern.

DETAILED DESCRIPTION OF PREFERRED EMBODIMENTS

Figure 1:
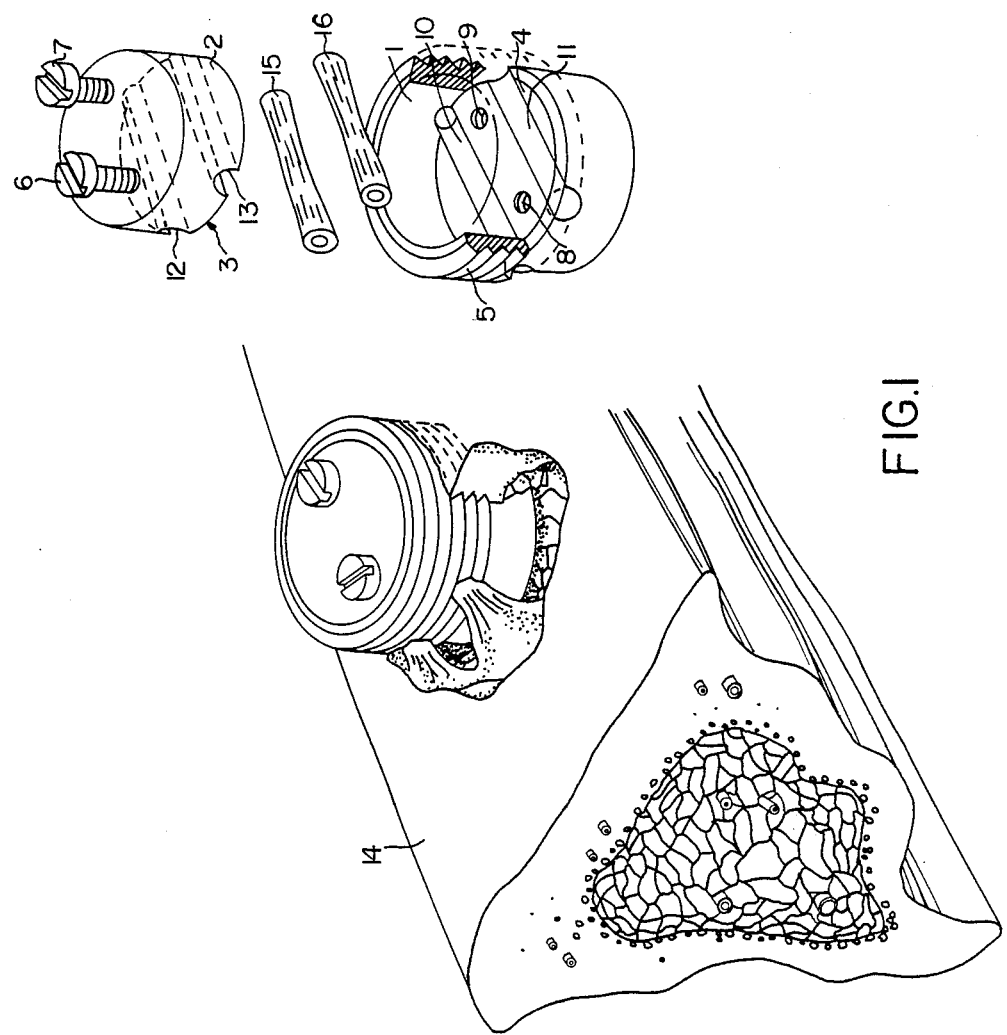

As was mentioned by way of introduction, the apparatus, hereinafter designated the implant, is based on the previously mentioned so-called Harvest Chamber. Thus, the implant consists of an outer cylindrical portion 1 of pure titanium and in which an inner, cylindrical portion 2 is inserted so that it rests with its lower end surface 3 on the bottom 4 of the outer portion. The outer cylindrical portion is provided with an external thread 5 for the careful threading in place of the implant in a bore in the bone tissue. Advantageously, use is made of the atraumatic insertion technique of the titanium implant which is previously known from Professor Brånemark's maxillary-anchored dental bridges and which constitutes a precondition for osseointegration. The inner, central portion 2 is locked to the outer portion by means of two locking screws 6 and 7 which are screwed in place in two threaded bottom holes 8 and 9 in the base plate 4. On its inner surface, the base plate has two grooves 10, 11 which cooperate with two corresponding grooves 12, 13 in the lower end surface of the central portion so that two through channels are formed for tissue growth when both of the portions 1 and 2 are assembled. Instead of causing the bone growth channels to be formed by cooperating grooves or grooved recesses in both the base plate and the central portion, the channels may be formed by grooves provided solely in the central portion, while the inner defining surface of the base plate is planar. In such instance, the grooves in the central recess may suitably be made somewhat deeper.

Once the implant has been surgically inserted in the bone tissue, for example in the tibia of a rabbit, a bone growth and healing process commences and the channels will duly be filled with newly-formed bone tissue. The bone formation process and the ingrown bone tissue may be studied at regular intervals when the central portion of the implant is removed.

Before the implantation, one of the channels is prepared with that test substance whose properties are to be examined. The test substance may be deposited in the channel by different means, for example, the channel may be doped with the test substance, the walls of the channel may be coated with the test substance etc. The implant is then inserted in, for example, the tibial metaphysis 14 of an experimental animal, it being ensured that the bone ingrowth channels are localized in the cortical bone. After the operation, the implant is covered with the soft tissue, skin and fascia which is sutured. After a bone ingrowth period of, for example, four weeks, the soft tissue is reopened, the locking screws are loosened and the central portion is removed. The newly-formed bone tissue in both channels, in the form of cylindrical rods 15, 16, are also removed. Evaluation of the results is effected in that the bone sample from the test substance channel is compared with the bone sample from the reference control channel. For quantification, use is made of data-based microradiography which is per se known and does not form part of the present invention, see for example the reference "The Harvest Chamber . . . " above.

Figure 2:
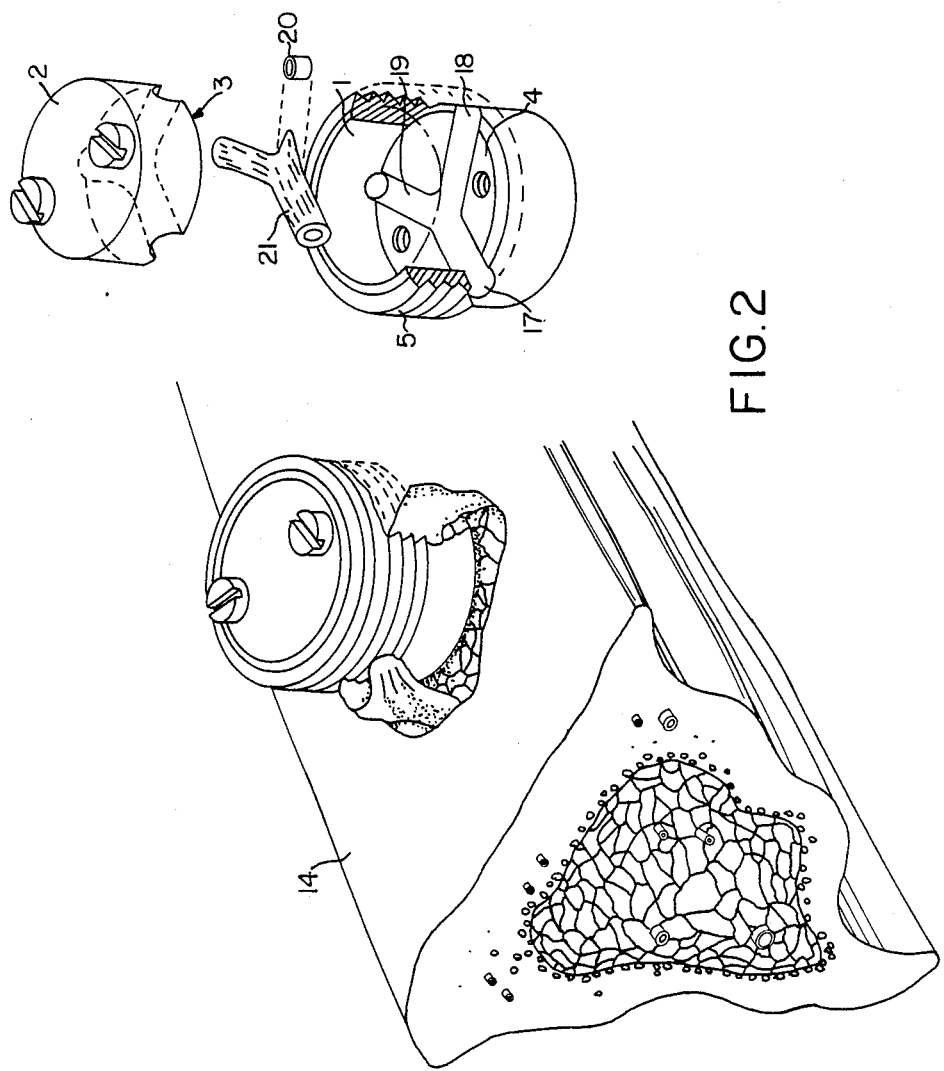

FIG. 2 illustrates an alternative embodiment of the present invention with three bone ingrowth channels 17, 18 and 19 which together form a Y. This configuration is particularly suited when different test substances are deposited through millipore filters 20. In such instance, the ends of each prong of the Y are closed by the millipore filters with the different substances which are to be tested. The implant is inserted in the same manner as that described above for the twin-channel chamber. After a suitable bone-ingrowth period, the implant is exposed, the central portion dismounted, the bone sample 21 is removed and the bone ingrowth in the three channels may be compared.

The present invention should not be considered as restricted to that described above and shown on the drawings, many modifications being conceivable without departing from, the spirit and scope of the appended claims.

What we claim and desire to secure by Letters Patent is:

1. An apparatus of a bio-compatible material for implantation in a living bone tissue and for studying bone tissue formation growth in an implant under different experimental conditions, said apparatus comprising:
   an outer portion with a central recess extending therethrough and a removable inner portion insertable in said central recess;
   means provided in at least a bottom wall of said outer portion cooperating with a bottom wall of said inner portion to form a plurality of bone tissue ingrowth channels when said inner portion is fully inserted into said central recess, said channels being exposable for access thereto when said inner portion is removed upwardly;
   wherein at least one of said channels, a test channel, is provided with a test substance, thereby allowing comparative examination of said bone tissue ingrowth in said cannels to determine promoting/retarding properties of said test substance on said bone tissue ingrowth.

2. The apparatus as claimed in claim 1, wherein said bone tissue ingrowth channels consist of two discrete through channels, one of the channels constituting said test channel, being provided with the test substance.

3. The apparatus as claimed in claim 2, wherein the test channel has been doped with the test substance.

4. The apparatus as claimed in claim 1, comprising three bone tissue ingrowth channels which form a Y-shaped pattern, whereby allowing comparison between properties of up to three different test substances disposed at the ends of each prong of the Y.

5. The apparatus as claimed in claim 4, wherein the ends of the prongs of the Y are closed by millipore filters.

* * * * *